(12) United States Patent
Spanswick et al.

(10) Patent No.: US 7,413,345 B1
(45) Date of Patent: Aug. 19, 2008

(54) CALIBRATION DEVICE AND METHOD OF USING SAME

(76) Inventors: Keith Spanswick, 20 Milton Drive, Ravenshead Nottingham, Notts, NG15-9BE, Nottingham, Notts. (GB) NG15-9BE; Paul Sunde, 11356 Baird Ave., Northridge, CA (US) 91326

( * ) Notice: Subject to any disclaimer, the term of this patent is extended or adjusted under 35 U.S.C. 154(b) by 0 days.

(21) Appl. No.: 11/786,575

(22) Filed: Apr. 11, 2007

(51) Int. Cl.
*G01D 18/00* (2006.01)

(52) U.S. Cl. .................. 378/207; 378/165; 378/166; 250/252.1

(58) Field of Classification Search .......... 378/97, 378/165, 166, 204–207; 250/252.1, 363.09, 250/385.1
See application file for complete search history.

(56) References Cited

U.S. PATENT DOCUMENTS 5,041,730 A * 8/1991 Attix .................. 250/385.1
2006/0266951 A1* 11/2006 Fritsch et al. .......... 250/385.1

* cited by examiner

*Primary Examiner*—Jurie Yun

(57) ABSTRACT

A calibration apparatus for the calibration of patient dose measurement and control systems of the character used in diagnostic radiology. The calibration apparatus includes a novel ion chamber that is of rigid construction. The ion chamber has a radiation input face that incorporates an optical alignment target or reticule having markings generally corresponding to a range of field sizes and shapes. A series of radio-opaque targets are embedded beneath the surface of the optical target to facilitate alignment using a radiation image.

20 Claims, 4 Drawing Sheets

CALIBRATION DEVICE AND METHOD OF USING SAME

BACKGROUND OF THE INVENTION

1. Field of the Invention

The present invention relates generally to calibration devices. More particularly, the invention concerns a device for the calibration of patient dose measurement and control systems of the character used in diagnostic radiology.

2. Discussion of the Prior Art

It is well known that overexposure of a patient to X-ray radiation can have serious adverse effects and should be minimized. Accordingly, it has long been recognized that some type of system for measuring the dose of X-ray radiation received by the patient is needed. In the past, dose-area product (DAP) has been measured in a number of different ways to evaluate the radiation exposure of the patient. The dose-area product of an X-ray beam may be defined as the surface integral of absorbed dose to air over a plane perpendicular to the beam.

Several prior art systems and devices, including DAP meters, have been proposed to measure DAP during diagnostic radiological procedures. In making these measurements, a full-field ionization chamber is typically mounted on the collimator face of the host equipment to measure the product of the air kerma or patient surface dose multiplied by the area of the radiation field. This measured dose area product, or KAP (kerma area-product) has the novel advantage of being a constant irrespective of distance from the radiation source.

The DAP, in combination with information on X-ray field size can be used to determine the average dose produced by the X-ray beam at any distance downstream in the X-ray beam from the location of the ionization chamber. DAP meters are usually calibrated approximating the integral by the product of the field area and the dose measured in the center of the field. However, the accuracy of this simplified method can be inadequate, especially when the meters are used for optimizing radiological procedures.

An alternative means of obtaining the dose area product is by calculation based on stored tables having data related to dose output at different X-ray generator kVp (kilo Voltage peak) and mAs (milli Amp seconds) settings. This data is multiplied by the radiation field area that is derived from collimator position sensing transducers.

Dose as opposed to dose area product is of greater interest when assessing local risk to organs including the skin as opposed to total body radiation burden. Dose can be obtained by mounting sensors on the patient's skin. However, this is generally considered to be excessively time consuming and inconvenient for routine use. An alternative approach is to measure the dose at the face of the collimator or calculate it based on machine settings and making corrections for the inverse square law relationship between doses measured at different distances from the radiation source.

In addition to the measurement of patient dose, it is increasingly common to control radiation exposure automatically. In this approach, a sensor is placed immediately in front of or to the rear of the image receptor, or dose related data is obtained directly from the image receptor output. In the past the objective of such devices was to optimize image quality. However, the emphasis is now directed toward the use of automatic control to ensure the dose used to produce an image is within appropriate reference levels.

At the present time, the common practice is for all equipment used for patient dose measurement and control to be calibrated during manufacture. This approach requires that the calibration be verified during equipment acceptance testing and at regular intervals during the life of host equipment. This calibration should ideally be referenced to the anticipated patient location and incorporate the influence of all objects in the beam-path including the table and the phantom that simulates the patient.

The current methods used to carry out such calibration checks involve measurement of central axis dose only and assessment of the field size based on image measurement. In addition to being extremely time consuming, such an approach is prone to both systemic and operator error.

As will better be appreciated from the discussion that follows the thrust of the present invention is to overcome the drawbacks of the prior art methods for carrying out calibration checks by providing a novel ion chamber having unique features that greatly simplify the testing and calibration of patient dose measurement and control devices.

SUMMARY OF THE INVENTION

By way of brief summary, one form of the apparatus of the present invention comprises an ion chamber that is of a rigid construction so as to, among other things, effectively eliminate volume changes resulting from temperature variations and mechanical stress. The ion chamber is uniquely designed to have a maximum measurement field size that is greater than the largest image size to be produced at the normal patient position. For convenience of handling, this maximum field size is in practice limited to approximately 30 cm by 30 cm.

To facilitate different settings of the collimator of the host equipment, in one form of the invention the radiation input-face of the chamber incorporates an optical alignment target or reticule having markings generally corresponding to a range of field sizes and shapes. Additionally, a series of radio-opaque targets are embedded beneath the surface of the optical target to facilitate alignment using a radiation image. This is particularly useful in those instances where the host equipment does not incorporate a light field. Further, the apparatus of the invention uniquely includes temperature and pressure transducers that are used to apply automatic correction factors to the measured ionization current.

In one form of the apparatus of the invention, a polarization potential power supply, an electrometer, a display and the necessary controls are incorporated in an extension of the ion chamber structure. In an alternate form of the invention, these components are housed in a separate housing that is interconnected with the ion chamber by a suitable connector cable.

In accomplishing one form of the method of the invention, approximate measurement of dose as opposed to dose area product can be achieved by dividing the dose area product measurement by the set field area. For more accurate dose measurement an absorber plate, having an aperture of known dimension, is placed on the face of the chamber.

In carrying out another form of the method of the invention, the ion chamber is used with a patient equivalent phantom that comprises a plurality of acrylic sheets, some of which incorporate inserts to simulate tissue of significantly different density such as lung and bone. Measurements can be conducted with the chamber mounted in front of the phantom to measure entrance dose or dose area product or behind the phantom to measure exit or image receptor dose or dose area product. Alternatively, measurements can be made at a specified point in space.

In addition to the measurement of dose, the chamber can be used to obtain "expected" optical or image density using a look-up table. To facilitate extensive processing of the measured dose, a computer interface is incorporated. By connecting the system to a computer, measurements can be displayed graphically, compared with reference levels and conveniently converted from dose area product to dose or optical density equivalence.

With the forgoing summary in mind, it is an object of the present invention to provide an apparatus of the character described that includes a readily transportable, mechanically rigid, radio-transparent ion chamber that can measure large field sizes.

Another object of the invention is to provide an apparatus of the aforementioned character for the calibration of patient dose measurement and control systems of the character used in diagnostic radiology that can be effectively and efficiently used with a minimum of operator training.

Another object of the invention is to provide a calibration apparatus that includes a full field ion chamber that incorporates optical aid, radio-transparent markers on the input-face of the chamber for alignment purposes.

Another object of the invention is to provide a calibration apparatus of the character described that includes automatic temperature and pressure correction of ion chamber current from integrated sensors.

Another object of the invention is to provide an apparatus of the character described that is of simple construction, can be inexpensively manufactured and is highly reliable in use.

Another object of the invention is to provide an apparatus of the character described in the preceding paragraphs that has an energy response, linearity with field size, dose rate and total dose that is significantly superior to the devices it is used to test.

Another object of the invention is to provide an apparatus of the type described that includes an ion chamber having rigid chamber walls that are constructed of a low atomic number material that has an electrode surface of high conductivity.

Another object of the invention is to provide an apparatus as described in the preceding paragraph in which the ion chamber is mounted on a substrate in a manner to effectively minimize leakage currents.

Another object of the invention is to provide an apparatus of the character described in the preceding paragraphs in which the ion chamber is capable of making measurements with greater or equal precision than those made by prior art devices, including methods for making measurements for determining DAP linearity vs. field size; DAP/Dose linearity vs. total dose; DAP/Dose linearity vs. dose-rate; DAP/Dose linearity with energy and DAP/Dose linearity with beam filtration.

Another object of the invention is to provide an apparatus of the character described in the preceding paragraphs, in which the ion chamber is capable of making measurements with greater or equal precision than those made by prior art devices, including methods for calibration of DAP Dose at a reference distance and field size; methods for entrance (skin) DAP and Dose calibration; and methods for exit (image receptor) DAP and Dose calibration.

Another object of the invention is to provide an apparatus of the type described that is capable of accomplishing precise automatic exposure control setting and assessment.

The foregoing, as well as other objects of the invention will be achieved by the methods and apparatus described in the following paragraphs.

DESCRIPTION OF THE INVENTION

Figure 1:
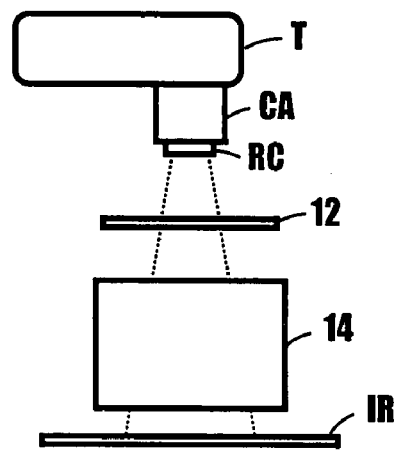
FIG. 1 is a generally diagrammatic view showing the calibration chamber of the apparatus of the invention positioned within an X-ray imaging system for dose or dose area product (DAP) calibration.
Figure 2:
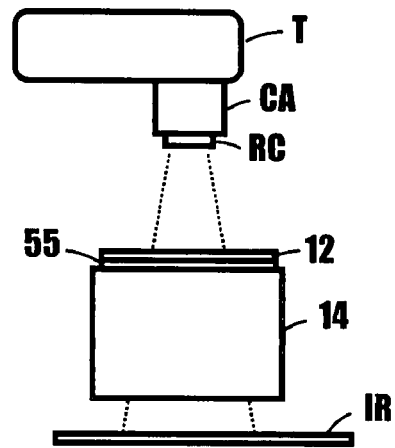
FIG. 2 is a generally diagrammatic view showing the calibration chamber of the apparatus positioned within an X-ray imaging system for entrance dose or DAP calibration.
Figure 3:
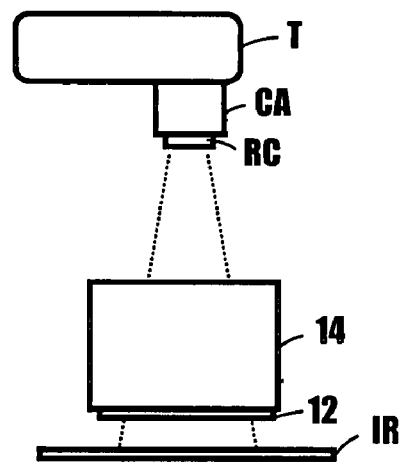
FIG. 3 is a generally diagrammatic view showing the calibration chamber of the apparatus of the invention positioned within an X-ray imaging system for image receptor dose or DAP calibration.

Referring to the drawings and particularly FIGS. 1, 2 and 3, one form of calibration chamber 12 is illustrated in various positions within an X-ray imaging system for performing various measurements. The X-ray imaging system, which is of a typical construction, includes an X-ray tube "T", a collimator assembly "CA", a resident chamber "RC" that is under test and image receptor "IR".

In FIG. 1 of the drawings, the apparatus is shown in position for performing dose or DAP calibration. In this instance, the calibration chamber 12 of the apparatus is located intermediate the resident chamber "RC" that is under test and a body equivalent phantom generally designated by the numeral 14. Phantom 14, the construction of which will be discussed in greater detail hereinafter, is here provided in the form a plurality of acrylic sheets that have substantially the same radiation absorption properties as tissue.

In FIG. 2 of the drawings the calibration chamber 12 is shown positioned directly on top of the body equivalent phantom 14 for performing entrance dose or DAP calibration. Similarly, in FIG. 3, the calibration chamber 12 is shown located between the body equivalent phantom 14 and the image receptor "IR" for performing image receptor dose or DAP calibration.

Figure 4:
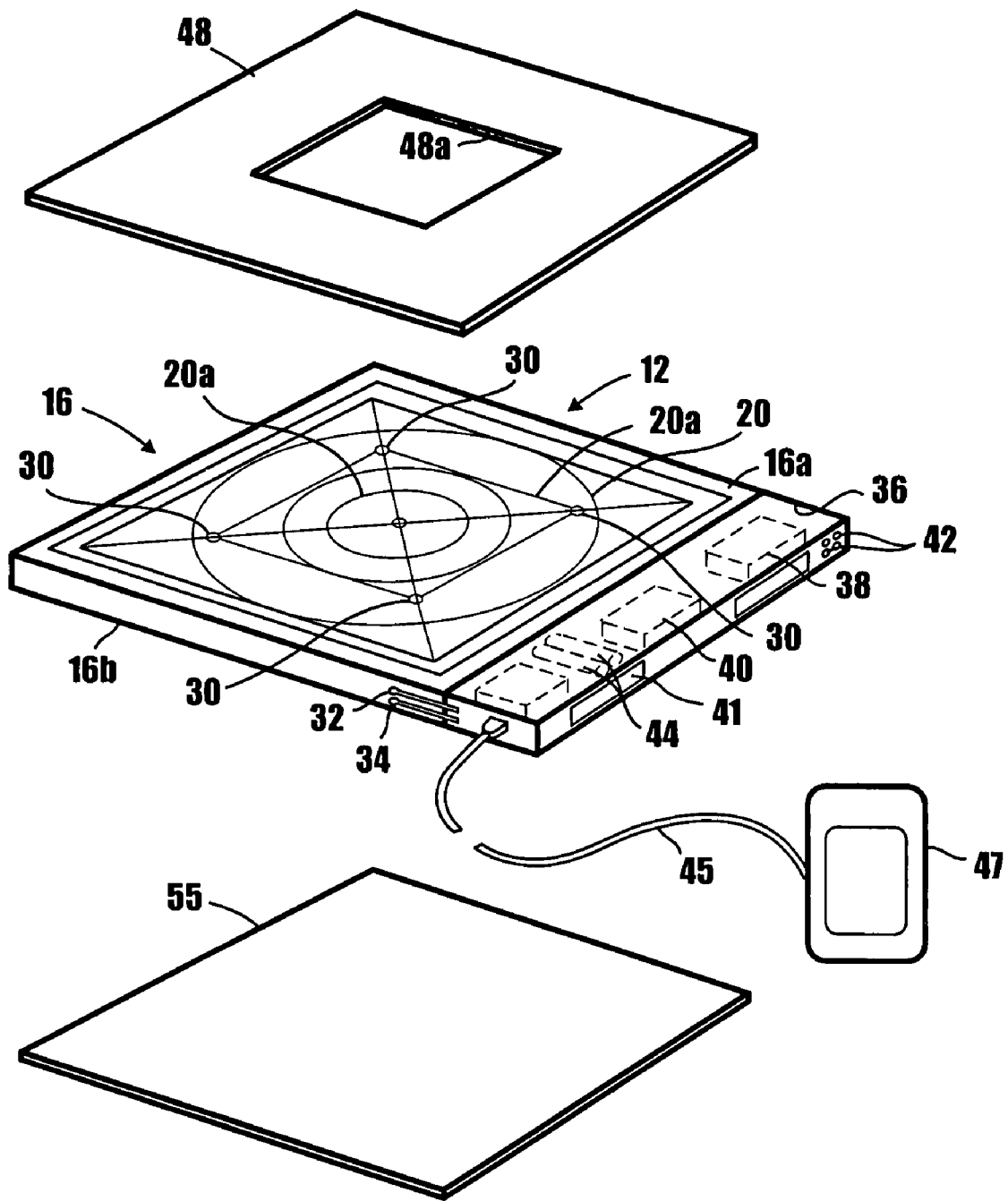
FIG. 4 is a generally perspective, exploded view of one form of the calibration apparatus of the present invention.
Figure 4A:
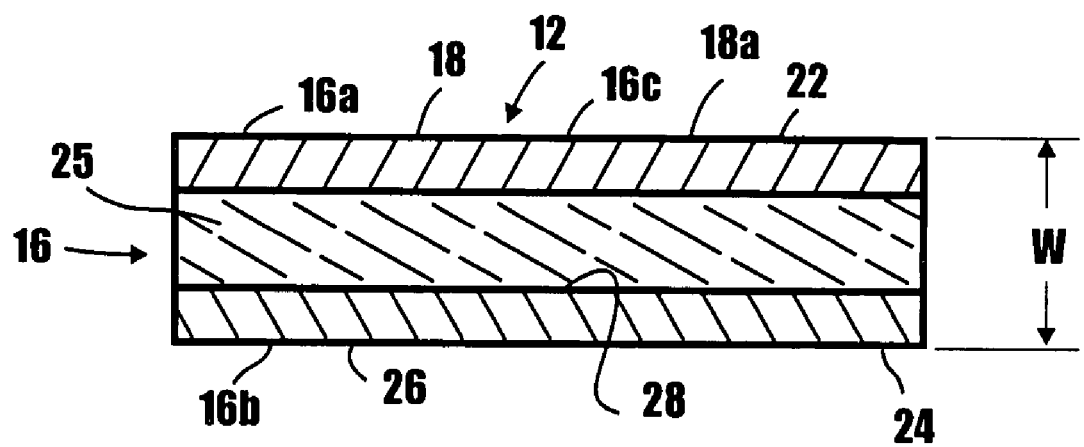
FIG. 4A is a transverse cross-sectional view of the apparatus shown in FIG. 4.

Turning particularly to FIGS. 4 and 4A of the drawings, the calibration chamber 12 can be seen to comprise an ion chamber that is of a rigid construction so as to, among other things, effectively eliminate volume changes resulting from temperature variations and mechanical stress. As previously mentioned, the ion chamber is uniquely designed to have a measurement field size of approximately 30 cm by 30 cm, which is typically greater than the largest image size to be produced at the normal patient position.

As shown in FIG. 4A, chamber 12 here comprises a housing 16 having upper and lower walls 16a and 16b that define therebetween an internal, unsealed chamber 16c. In the present embodiment of the invention, upper wall 16a comprises a novel optical marker sheet 18 having on its upper surface 18a an optical alignment target or reticule 20, which uniquely comprises markings 20a that generally correspond to a range of field sizes and shapes (see FIG. 4).

Spaced-apart from upper wall 16a is a carbon fiber signal electrode 22. Disposed between upper wall 16a and electrode 22 is an insulating foam filler 24 formed from a material, such as polystyrene. Spaced-apart from lower wall 16b by an insulating foam filler 25 formed from a material, such as polystyrene, is a carbon fiber, high-voltage plate 26 (FIG. 4A). As indicated in FIG. 4A, the gap 28 between electrode 22 and plate 26 contains air at atmospheric pressure, thereby providing automatic correction for air density due to temperature and pressure changes. It is to be understood that, although carbon fiber materials provide a rigid, conducting and stable construction for electrode 22 and plate 26, other non-naturally conducting materials can be used and their surfaces coated or painted with commonly available conducting graphite materials.

An important feature of the present invention resides in the provision of a series of radio-opaque targets 30 that are embedded beneath the surface of the optical target to facilitate alignment and calibration of the light field using a radiation image. These opaque targets are particularly useful in those instances where the host equipment does not incorporate a light field.

As best seen in FIG. 4, the apparatus of the invention also includes temperature and pressure transducers 32 and 34 that are used to apply automatic correction factors to the measured ionization current. In the form of the invention shown in FIG. 4a the apparatus includes an extension chamber 36 that houses a conventional polarization potential power supply 38, a conventional electrometer 40 and necessary controls 42 which are of a character well understood by those skilled in the art and are readily commercially available. Also provided on extension chamber 36 is a suitable display 44 which is also readily commercially available.

Interconnected with extension chamber 36 by an appropriate cable 45 and operably associated with electrometer 40 is a conventional, readily commercially available computer 47. Computer 47 can be programmed in a manner well understood by those skilled in the art to analyze and display the data generated by the electrometer 40.

Figure 5:
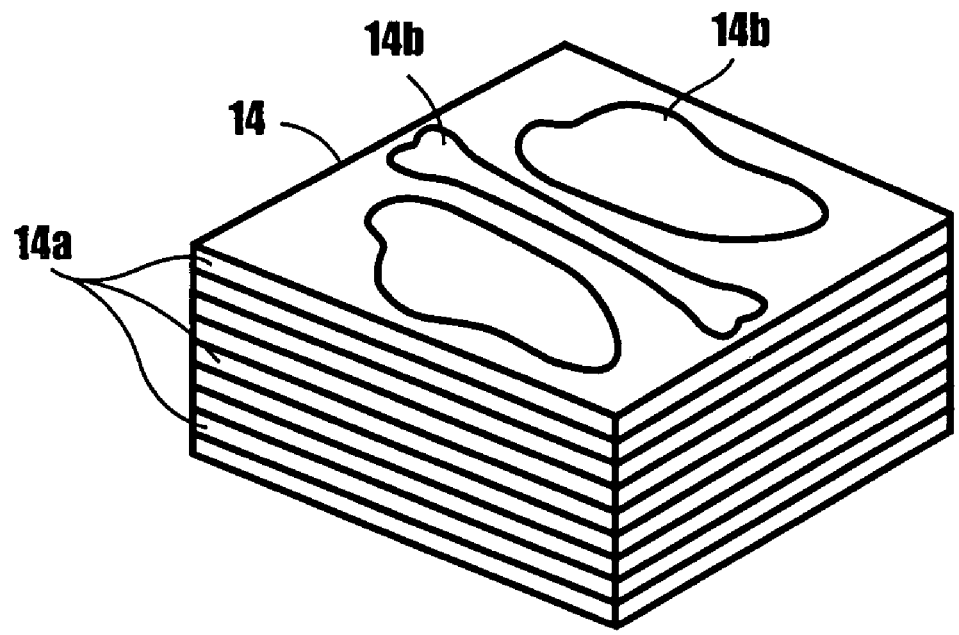
FIG. 5 is a generally perspective view of a patient equivalent phantom of the character that can be used in connection with the calibration apparatus of the invention.
Figure 6:
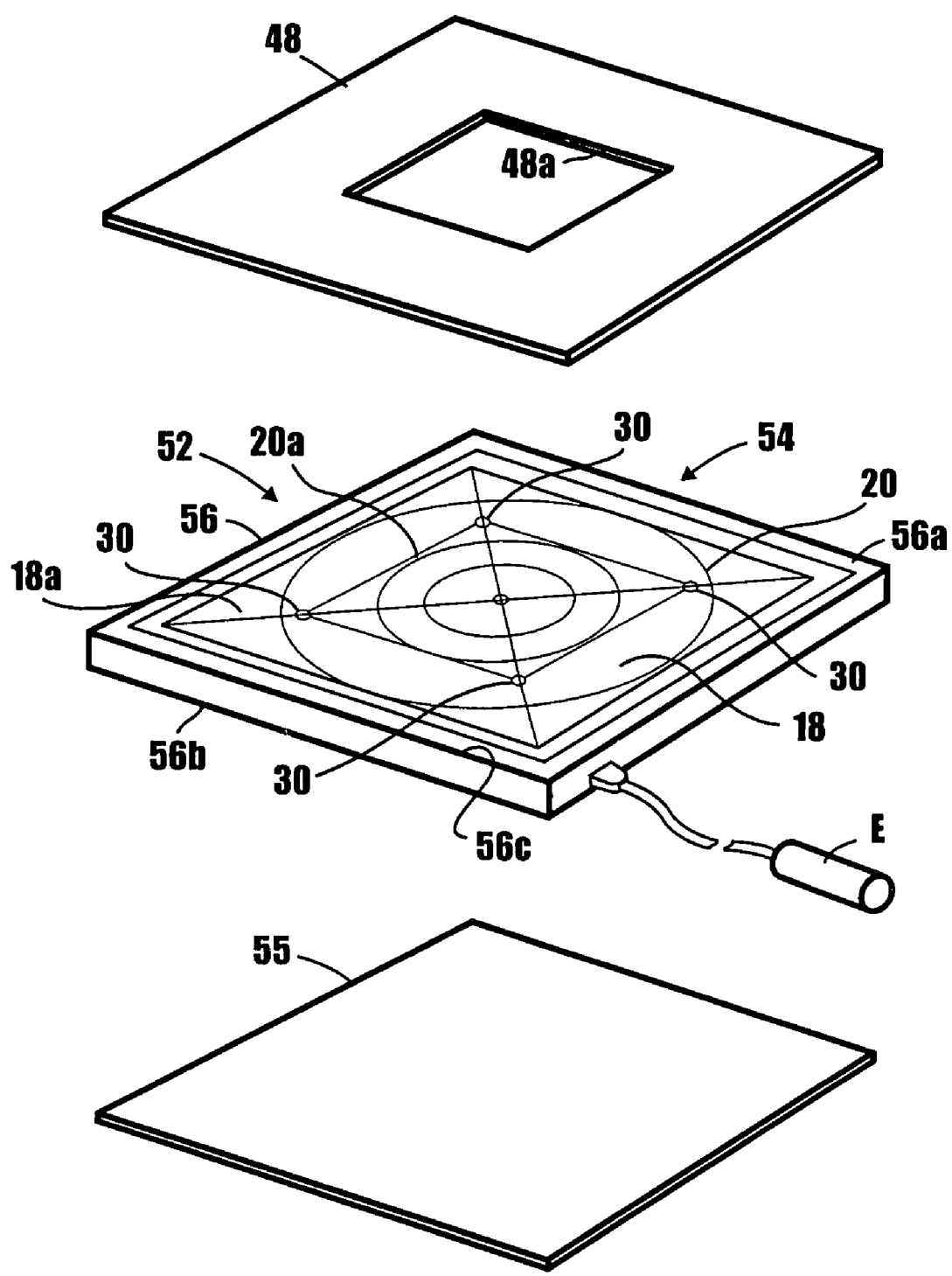
FIG. 6 is a generally perspective, exploded view of an alternate form of calibration apparatus of the present invention.

Referring next to FIG. 6, an alternate form of the apparatus of the invention is there shown and generally designated by the numeral 52. This apparatus is similar in many respects to that illustrated in FIGS. 1 through 5 and like numerals are used in FIG. 6 to identify like components. The primary difference between this latter form of the invention and the earlier described embodiment resides in the fact that the apparatus does not have any attached readout capability. Rather, as will be discussed more fully hereinafter, the chamber is connected to an electrometer and an appropriate high-voltage power supply. In using this latest embodiment of the invention, the user reads the electrometer and applies appropriate calibration and correction factors to determine the dose and DAP.

As before, the apparatus of this alternate form of the invention includes a novel calibration chamber 54 that can be located in the various positions illustrated in FIGS. 1, 2 and 3. As depicted in FIG. 6, chamber 54 here comprises a housing 56 having upper and lower walls 56a and 56b that define therebetween an internal, unsealed chamber 56c. As in the earlier described embodiment, upper wall 56a comprises a novel optical marker sheet 18 having on its upper surface 18a an optical alignment target or reticule 20 which uniquely comprises markings 20a that generally correspond to a range of field sizes and shapes (see FIG. 6).

Spaced-apart from upper wall 56a is a carbon fiber signal electrode. Disposed between upper wall 56a and electrode 22 is an insulating foam filler, such as the earlier described filler 24. Spaced-apart from lower wall 56b by an insulating foam filler, such as filler 25, is a carbon fiber, high-voltage plate 26 (FIG. 4A). As before, the gap between electrode 22 and plate 26 contains air and atmospheric pressure, thereby providing automatic correction for air density due to temperature and pressure changes.

This latest form of the invention also includes the important series of radio-opaque targets 30 that are embedded beneath the surface of the optical target to facilitate alignment using a radiation image.

As indicated in FIG. 6, the apparatus of this latest form of the invention is connected to a conventional electrometer "E" and a conventional high voltage bias supply. As previously mentioned, in using this latest embodiment of the invention, the user reads the electrometer and then in a manner well understood by those skilled in the art, applies appropriate calibration and correction factors to determine the dose and DAP.

In the normal operation of the X-ray imaging system the patient is placed between the X-ray tube and the image receptor. The X-ray tube is then energized, typically by an external controller. The X-ray tube emits X-rays which pass through the collimator, through the patient and are received by the image receptor. The image receptor then interprets the intensity of the received X-rays to produce an X-ray image of the patient.

In accomplishing one form of the method of the invention, the ion chamber 12 of the calibration apparatus of the invention is positioned in free space between the image receptor and the collimator to perform dose or dose DAP calibration (see FIG. 1).

In another form of the method of the invention for accomplishing entrance dose or DAP calibration, the ion chamber of the calibration apparatus is used with the patient equivalent phantom 14, which, as shown in FIG. 5, comprises a plurality of acrylic sheets, some of which incorporate inserts to simulate tissue of significantly different density such as lung and bone. As depicted in FIG. 2, these measurements are conducted with the ion chamber 12 mounted in front of the phantom to measure entrance dose or dose area product or behind the phantom to measure exit or image receptor dose or dose area product.

Generally the phantom 14 is intended to mimic certain properties of the human body. A variety of different phantoms such as are well known in the art, may be used in place of the phantom 14 as herein described, provided their geometry and composition may be accurately characterized.

In still another form of the method of the invention for accomplishing image receptor dose or DAP calibration, the ion chamber 12 of the apparatus of the invention is positioned between the phantom and the image receptor (see FIG. 3).

In yet another form of the method of the invention an approximate measurement of dose as opposed to dose area product is achieved by dividing the dose area product measurement by the set field area. For more accurate dose measurement an absorber plate 48, with an aperture 48a of known dimension, is placed on the face of the chamber (see FIG. 4).

In addition to the measurement of dose, the chamber can be used to obtain "expected" optical or image density using a look-up table. To facilitate extensive processing of the measured dose, a computer interface is incorporated. By connecting the system to a computer 55 in the manner depicted in FIG. 4, measurements can be displayed graphically, compared with reference levels and conveniently converted from dose area product to dose or optical density equivalence.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A calibration apparatus for the calibration of patient dose measurement and control systems of the character used in diagnostic radiology, said apparatus including a radio-transparent, mechanically rigid ion chamber comprising:
   (a) a housing having an upper wall and a spaced-apart lower wall defining a chamber therebetween;
   (b) an optical alignment target provided on said upper wall; and
   (c) a plurality of optical-aid radio-transparent alignment markers mounted on said upper wall.

2. The apparatus as defined in claim 1 in which said radio-transparent, mechanically rigid ion chamber further comprises a temperature transducer carried by said housing.

3. The apparatus as defined in claim 1 in which said radio-transparent, mechanically rigid ion chamber further comprises a pressure transducer carried by said housing.

4. The apparatus as defined in claim 1 in which said radio-transparent, mechanically rigid ion chamber further comprises an apertured absorber plate overlaying said upper wall.

5. The apparatus as defined in claim 1 in which said radio-transparent, mechanically rigid ion chamber further comprises an air gap between said upper and lower walls.

6. The apparatus as defined in claim 1 in which said radio-transparent, mechanically rigid ion chamber further comprises a conductive signal electrode spaced-apart from said upper wall.

7. The apparatus as defined in claim 6 in which said radio-transparent, mechanically rigid ion chamber further comprises a foam filler disposed between said conductive signal electrode and said upper wall.

8. The apparatus as defined in claim 6 in which said radio-transparent, mechanically rigid ion chamber further comprises a high voltage plate spaced-apart from said lower wall.

9. The apparatus as defined in claim 8 in which said radio-transparent, mechanically rigid ion chamber further comprises a foam filler disposed between said high voltage plate and said lower wall.

10. An apparatus for use with an X-ray imaging system for measuring dose area product, including a radio-transparent, mechanically rigid ion chamber comprising:
    (a) a housing having an upper input-face and a spaced-apart lower wall defining a chamber therebetween;
    (b) an optical alignment target provided on said input-face; and
    (c) a plurality of optical-aid radio-transparent alignment markers mounted on said input-face;
    (d) an electrometer disposed within said chamber;
    (e) a temperature transducer carried by said housing;
    (f) a pressure transducer carried by said housing; and
    (g) a computer operably associated with said electrometer, said temperature transducer and said pressure transducer.

11. The apparatus as defined in claim 10 in which said radio-transparent, mechanically rigid ion chamber further comprises an apertured absorber plate overlaying said upper input-face.

12. The apparatus as defined in claim 10 in which said radio-transparent, mechanically rigid ion chamber further comprises a conductive signal electrode spaced-apart from said input-face.

13. The apparatus as defined in claim 12 in which said radio-transparent, mechanically rigid ion chamber further comprises a high voltage plate spaced-apart from said lower wall.

14. The apparatus as defined in claim 13 in which said radio-transparent, mechanically rigid ion chamber includes an air gap containing air at atmospheric pressure, said air gap being disposed between said signal electrode and said high voltage plate.

15. A method for performing calibration measurements within an X-ray imaging system that includes an X-ray tube, a collimator assembly, a resident chamber that is under test and an image receptor using a calibration apparatus that includes a radio-transparent, mechanically rigid ion chamber comprising a housing having an upper input-face provided with an optical alignment target and a plurality of optical-aid radio-transparent alignment markers, said method comprising the step of strategically positioning the radio-transparent, mechanically rigid ion chamber between the collimator assembly and the image receptor.

16. The method as defined in claim 15 in which the calibration apparatus further comprises a body equivalent phantom positioned proximate the image receptor and in which the radio-transparent, mechanically rigid ion chamber is positioned on the body equivalent phantom to perform entrance dose calibration.

17. The method as defined in claim 15 in which the calibration apparatus further comprises a body equivalent phantom positioned proximate the image receptor and in which the radio-transparent, mechanically rigid ion chamber is positioned between the body equivalent phantom and the image receptor to perform image receptor dose calibration.

18. The method as defined in claim 15 in which the calibration apparatus further comprises a body equivalent phantom positioned proximate the image receptor and in which the radio-transparent, mechanically rigid ion chamber is positioned between the resident chamber under test and the body equivalent phantom to perform dose air calibration.

19. The method as defined in claim 15 in which the calibration apparatus further comprises an apertured absorber plate and in which the method comprises the further step of positioning the apertured absorber plate over the radio-transparent, mechanically rigid ion chamber.

20. The method as defined in claim 15 in which the calibration apparatus further comprises an electrometer and a high-voltage power supply and in which the method comprises the further step of reading the electrometer and then applying calibration and correction factors to determine the dose and DAP.

* * * * *